(12) United States Patent
Barnard et al.

(10) Patent No.: US 8,207,364 B2
(45) Date of Patent: Jun. 26, 2012

(54) PROCESS FOR PREPARING A COMPLEX

(75) Inventors: Christopher Francis James Barnard, Henley-on-Thames (GB); Hongbo Li, Thorofare, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 12/787,795

(22) Filed: May 26, 2010

(65) Prior Publication Data

US 2010/0305349 A1 Dec. 2, 2010

Related U.S. Application Data

(60) Provisional application No. 61/181,087, filed on May 26, 2009.

(51) Int. Cl.
C07F 15/00 (2006.01)

(52) U.S. Cl. ............................................. 556/20; 556/21

(58) Field of Classification Search .................... 556/20, 556/21

See application file for complete search history.

(56) References Cited

U.S. PATENT DOCUMENTS

| | | | |
|---|---|---|---|
| 6,268,527 B1 | 7/2001 | Koide et al. | |
| 2004/0167259 A1 | 8/2004 | Schmid et al. | |
| 2006/0264558 A1 | 11/2006 | Schmid et al. | |

FOREIGN PATENT DOCUMENTS

| | | |
|---|---|---|
| EP | 1 857 487 A1 | 11/2007 |
| WO | WO-01/16260 A1 | 3/2001 |
| WO | WO-02/48094 A1 | 6/2002 |

OTHER PUBLICATIONS

Maier, "Organische Phosphorverbindungen XXII. Darstellung und Eigenschaften von diprimären α,ω-Bis-Phosphino-alkanen," *Helvetica Chimica Acta*, 1966, vol. 49, No. 2, pp. 842-851.
Tani et al., "Mechanistic Aspects of Catalytic Hydrogenation of Ketones by Rhodium(I)-Peralkyldiphosphine Complexes," *Journal of Organometallic Chemistry*, 1985, vol. 279, pp. 87-101.
Lindner et al., "Catalytic activity of cationic diphospalladium(II) complexes in the alkene/CO copolymerization in organic solvents and water in dependence on the length of the alkyl chain at the phosphine ligands," *Journal of Organometallic Chemistry*, 2000, vol. 602, pp. 173-187.
Csákai et al., "NMR investigation of PD(II)-PD(0) reduction in the presence of mono- and ditertiary phosphines," *Inorganica Chimica Acta*, 1999, vol. 286, pp. 93-97.
Hewertson et al., "The Preparation of Di- and Tri-tertiary Phosphines," *Journal of the Chemical Society*, 1962, pp. 1490-1494.
Fryzuk et al., "Reactivity of Electron-Rich Binuclear Rhodium Hydrides. Synthesis of Bridging Alkenyl Hydrides and X-ray Crystal Structure of $[\{((CH_3)_2CH)_2PCH_2CH_2P(CH(CH_3)_2)_2\}Rh]_2(\mu\text{-H})(\mu\text{-}\eta^2\text{-CH=CH}_2)$," *Organometallics*, 1984, vol. 3, No. 2, pp. 185-191.
Morris et al., "Modification of ligand properties of phosphine ligands for C—C and C—N bond-forming reactions," *Tetrahedron Letters*, 2007, vol. 48, No. 6, pp. 949-953.
Wang et al., "Transfer-dehydrogenation of alkanes catalyzed by rhodium(I) phosphine complexes," *Journal of Organometallic Chemistry*, 1996, vol. 518, No. 1, pp. 55-68.
Werner et al., "A New Synthetic Route to Unsymmetrical 1,2-Bis(phosphanyl)ethanes with and 1,2-Arsanyl(phosphanyl)ethanes with and without a Stereogenic Center," *Angew. Chem. Int. Ed.*, 2000, vol. 39, No. 3, pp. 564-566.
Fryzuk et al., "Coordinatively unsaturated binuclear clusters of rhodium. The reactivity of $[\{Pr^i_2P(CH_2)_nPPr^i2\}Rh]_2(\mu\text{-H})_2$ (n=2,3, and 4) with dihydrogen, and their use in the catalytic hydrogenation of olefins," *Can. J. Chem.*, 1989, vol. 67, pp. 883-896.
Raebiger et al., "Using Ligand Bite Angle to Control the Hydricity of Palladium Diphosphine Complexes," *J. Am. Chem. Soc.*, 2004, vol. 126, pp. 5503-5504.
International Search Report dated Sep. 15, 2010, from PCT International Application No. PCT/GB2010/050860.
International Preliminary Report on Patentability dated Nov. 29, 2011, from PCT International Application No. PCT/GB2010/050860.

*Primary Examiner* — Porfirio Nazario Gonzalez
(74) *Attorney, Agent, or Firm* — RatnerPrestia

(57) ABSTRACT

The present invention provides a process for the preparation of a complex of formula (A) or (B):

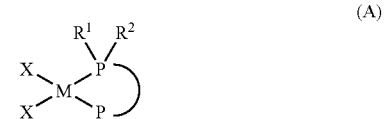

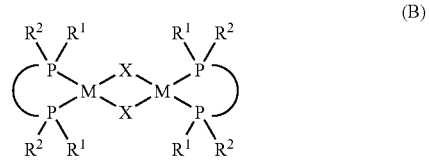

wherein,

M is a platinum group metal atom;

each X is an anionic monodentate ligand;

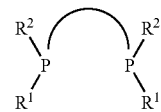

is a bidentate phosphine ligand; and $R^1$ and $R^2$ are independently selected from the group consisting of straight-chain $C_{1-10}$ alkyl, branched-chain $C_{3-10}$ alkyl, $C_{3-10}$ cycloalkyl and optionally substituted aryl;

comprising the steps of:

(a) preparing

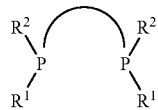
by reacting the lithium salt of $R^1R^2PH$ with a dihaloalkane in a solvent comprising an alkyl ether and, optionally, an alkane, provided the alkyl ether is not diethyl ether;
(b) reacting
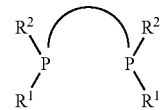
with a platinum group metal precursor compound to form the complex of formula (A) or formula (B).
14 Claims, No Drawings

PROCESS FOR PREPARING A COMPLEX

CROSS-REFERENCE TO RELATED APPLICATIONS

This application claims priority from U.S. Provisional Application No. 61/181,087, filed May 26, 2009, the disclosure of which is incorporated herein by reference in its entirety for all purposes.

FIELD OF THE INVENTION

The present invention concerns the preparation of metal complexes, in particular complexes which are useful in carbonylation reactions.

BACKGROUND OF THE INVENTION

Compounds of the type $PdX_2(PR_2(CH_2)_nPR_2)$ are preferred catalysts for many types of carbonylation reactions of aryl and vinyl halides and sulfonates. As with many other organometallic compounds the standard method of preparation for these compounds is to prepare, isolate and purify the phosphine ligand and react it with a suitable metal precursor. A major part of such preparations is the isolation and purification of the phosphine ligand. The ligand itself may be highly reactive and likely to suffer from oxidation, yielding the unreactive phosphine oxide as an impurity, so additional precautions such as the formation of an acid salt (e.g. using $HBF_4$) are needed to stabilise the ligand for storage and ease of handling.

There are few examples of preparative procedures for ligands $PR_2(CH_2)PR_2$ in the literature. One example relates to the preparation of $^iPr_2P(CH_2)_3P^iPr_2$ (K. Tani et al, J. Organometallic Chem. 1985, 279, 87-101). The method recommends the reflux of a reaction mixture comprising ether and n-hexane as solvents for the completion of the reaction before the removal of solvents and distillation to isolate the product. The present inventors have found, however, that thermal decomposition of the product during distillation reduces the overall yield.

Alternative routes to these compounds exist, such as the photochemical hydrophosphination of primary phosphines $H_2P(CH_2)_3PH_2$ reported by Maier (Helvetica Chimica Acta, 1966, 49, 842) and Lindner et al (J. Organometallic Chem., 2000, 602, 173). This method is not applicable to all diphosphines and the latter group also report the preparation via $Cl_2P(CH_2)_3PCl_2$ by reaction with Grignard reagents to yield alkyl-substituted diphosphines (J. Organometallic Chem., 2000, 602, 173). However, these methods involve complex, often multi-step preparation and purification procedures and yield highly air-sensitive products.

Typical routes for the formation of Pd complexes are described by Lindner et al (J. Organometallic Chem., 2000, 602, 173). Combination of the diphosphine ligand with a palladium precursor such as $PdCl_2(PhCN)_2$ yields $PdCl_2(R_2P(CH_2)_nPR_2)$. Reaction with $Pd(OAc)_2$ can be used to prepare acetate complexes, although these compounds are reported to slowly decompose after the removal of solvents (Lindner et al., J. Organometallic Chem., 2000, 602, 173 and Z. Csakai et al., Inorg. Chim. Acta 1999, 286, 93).

SUMMARY OF THE INVENTION

The present inventors have now found that such complexes may be conveniently prepared without the isolation of the ligand. Efforts to adopt such procedures for the preparation of organometallic compounds have often proved ineffective due to incompatibilities between the various reagents. A method to avoid this has been developed using the synthesis described below. Through the method described, the ligand is prepared in high yield, excess reagents and by-products may be removed, and the ligand solution may then be conveniently reacted with a metal precursor solution to yield the desired catalyst.

DETAILED DESCRIPTION OF THE INVENTION

Accordingly, the present invention provides a process for the preparation of a complex of formula (A) or (B):

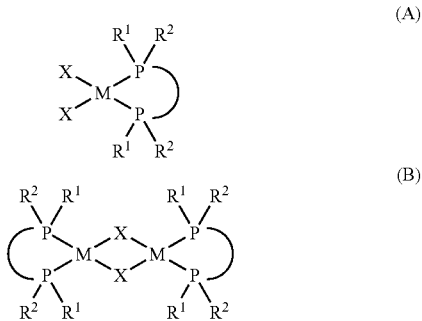

wherein,
M is a platinum group metal atom;
each X is an anionic monodentate ligand;

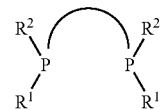

is a bidentate phosphine ligand; and
$R^1$ and $R^2$ are independently selected from the group consisting of straight-chain $C_{1-10}$ alkyl, branched-chain $C_{3-10}$ alkyl, $C_{3-10}$ cycloalkyl and optionally substituted aryl;
comprising the steps of:
(a) preparing

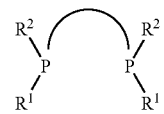

by reacting the lithium salt of $R^1R^2PH$ with a dihaloalkane in a solvent comprising an alkyl ether and, optionally, an alkane, provided the alkyl ether is not diethyl ether;
(b) reacting

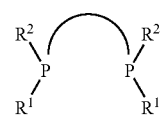

with a platinum group metal (PGM) precursor compound to form the complex of formula (A) or formula (B).

The platinum group metal atom M is preferably selected from the group consisting of ruthenium, rhodium, palladium, osmium, iridium and platinum. More preferably, M is selected from the group consisting of rhodium, palladium, iridium and platinum.

Each X is an anionic monodentate ligand which may be independently bonded in either a terminal or bridging mode. Preferably, each X is independently selected from the group consisting of chloride, bromide, iodide and acetate.

The bidentate phosphine ligand is prepared from the lithium salt of a secondary phosphine $R^1R^2PH$ i.e. $R^1R^2PLi$. $R^1$ and $R^2$ are independently selected from the group consisting of straight-chain $C_{1-10}$ alkyl, branched-chain $C_{3-10}$ alkyl, $C_{3-10}$ cycloalkyl and optionally substituted aryl. The optionally substituted aryl may have substituents which are preferably selected from the group consisting of straight-chain $C_{1-10}$ alkyl, branched-chain $C_{3-10}$ alkyl, $C_{3-10}$ cycloalkyl and $NR^3R^4$. $R^3$ and $R^4$ are independently selected from the group consisting of straight-chain $C_{1-10}$ alkyl, branched-chain $C_{3-10}$ alkyl and $C_{3-10}$ cycloalkyl (for example, methyl, ethyl, n-propyl, i-propyl, n-butyl, i-butyl, t-butyl, cyclopentyl, cyclohexyl or norbornyl).

$R^1$ and $R^2$ may be the same or different and are preferably the same. In one embodiment, $R^1$ and $R^2$ are independently selected from the group consisting of methyl, ethyl, n-propyl, i-propyl, n-butyl, i-butyl, t-butyl, cyclopentyl, cyclohexyl, norbornyl and phenyl. More preferably, $R^1$ and $R^2$ are independently selected from the group consisting of i-propyl, i-butyl, t-butyl, cyclopentyl, cyclohexyl, norbornyl and phenyl.

The lithium salt of $R^1R^2PH$ may be prepared using methods known to the skilled person. For example, $R^1R^2PH$ may be reacted with an alkyl lithium reagent, such as n-BuLi or sec-BuLi, at a suitable concentration to form $R^1R^2PLi$. The alkyl lithium reagent may be conveniently purchased as a solution in a solvent, such as hexane. The reaction between the alkyl lithium reagent and $R^1R^2PH$ is normally complete within about 0 to about 60 minutes and typically within about 30 minutes. The reaction mixture is optionally stirred for a further period of time of up to about 60 minutes and is optionally cooled before the lithium salt is combined with the dihaloalkane. When the reaction is conducted on a large scale it is preferable that the reaction mixture is cooled (e.g. with an ice/water bath) to avoid warming as a result of the exothermic reaction. Preferably, the reaction is conducted under an inert atmosphere, such as nitrogen or argon.

The dihaloalkane preferably has the formula $Hal-(CR^5R^6)_m-Hal$ wherein Hal is a halide, preferably, chloride, bromide or iodide, m is 2, 3 or 4, and $R^5$ and $R^6$ are independently selected from the group consisting of H, straight-chain $C_{1-10}$ alkyl, branched-chain $C_{3-10}$ alkyl, and $C_{3-10}$ cycloalkyl. In one embodiment, the dihaloalkane is preferably 1,3-dichloropropane, 1,4-dichlorobutane or 1,3-dichlorobutane. In this instance, therefore, m is 3 or 4.

The lithium salt of $R^1R^2PH$ and the dihaloalkane are combined in a solvent comprising an alkyl ether and, optionally, an alkane, provided the alkyl ether is not diethyl ether. Preferably, the alkyl ether is anhydrous. In one embodiment, the alkyl ether is a cyclic alkyl ether and more preferably tetrahydrofuran (THF). In another embodiment, the alkyl ether is methyl tert-butyl ether (MTBE). With regard to THF and MTBE, the use of alkyl ethers such as these is advantageous as THF and MTBE have higher flashpoint temperatures giving improved safety in handling.

Suitable alkanes have boiling points at atmospheric pressure between 0 to 150° C. The alkane is preferably anhydrous. Alkanes that may be used are low boiling alkanes such as pentane isomers, hexane isomers, heptane isomers or octane isomers. Preferably, the alkane is n-pentane, n-hexane or n-heptane.

The components may be mixed in any suitable order, although it is preferred that the dihaloalkane is added to a mixture of $R^1R^2PLi$ and the solvent as $R^1R^2PLi$ is often present as a precipitate. Preferably, the mixture is stirred for about 10 minutes to about 24 hours. Preferably, the reaction is conducted under an inert atmosphere, such as nitrogen or argon.

In one embodiment, the reaction is preferably carried out at one or more temperatures between about −10° C. and about 40° C., in another embodiment, between about −10° C. and about 35° C. and, in yet another embodiment, between about −10° C. and about 30° C. Studies of reaction mixtures comprising $R^1R^2PLi$ and the dihaloalkane using $^{31}P$ NMR showed that formation of the diphosphine surprisingly occurs readily and cleanly at room temperature, indicating that impurities are formed on heating, which lead to reduced yield and formation of impurities in subsequent preparative steps. When the dihaloalkane is added to a mixture of $R^1R^2PLi$ and the solvent, therefore, the rate of addition is controlled in order to limit the temperature increase due to the exothermic reaction. Accordingly, when the reaction is conducted on a large scale, it is preferable that the reaction mixture is cooled (e.g. using an ice/water bath).

Once the bidentate phosphine ligand has been prepared, the reaction mixture obtained after step (a) may be reacted directly with the PGM precursor compound, although the presence of unwanted by-products, as well as the presence of excess alkyl lithium reagent, may result in contamination and a reduced yield of the complex of formula (A) or (B).

In one embodiment, the reaction mixture obtained after step (a) may be treated one or more times with water (preferably degassed water) and the aqueous layer(s) discarded. The treatment with water is advantageous as the unwanted by-products are removed with the aqueous layer(s) and the excess alkyl lithium reagent is destroyed, thus preventing reduction of the PGM precursor compound. In this embodiment, the amount of the alkyl lithium reagent is preferably in excess of the $R^1R^2PH$, thus avoiding an excess of expensive $R^1R^2PH$. Preferably, the molar ratio of the alkyl lithium reagent to $R^1R^2PH$ is $\geq 1:1$ and in one embodiment is about 1.07:1. After the water wash, the remaining organic layer may then be combined with the PGM precursor compound if desired.

In another embodiment, the amount of the $R^1R^2PH$ is preferably in excess of the alkyl lithium reagent. This advantageously avoids an excess of alkyl lithium reagent with the result that the degradation of the PGM metal precursor compound is reduced. In addition, as no free alkyl lithium reagent is present, the water wash described above becomes unnecessary and the separation of phases is thus avoided. The process therefore becomes more volume efficient allowing a better throughput for manufacturing. Preferably, the molar ratio of the $R^1R^2PH$ to alkyl lithium reagent is 1:1, more preferably $\geq 1.1:1$ and most preferably about 1.2:1. In this embodiment, the reaction mixture obtained after step (a) may be filtered through Celite™ and then added to the PGM precursor compound.

Whether the water wash or the use of excess $R^1R^2PH$ is chosen will depend on the economics of a particular process. However, regardless of the actual method selected, the avoidance of the need to isolate the pure bidentate phosphine ligand (for example, using vacuum distillation) makes these processes cost competitive.

Alternatively, the bidentate phosphine ligand may be isolated and, if necessary, purified using conventional methods before reacting the ligand with the PGM precursor compound.

The PGM precursor compound is reacted with the bidentate phosphine ligand to form the complex of formula (A) or formula (B). Preferably, the reaction is conducted under an inert atmosphere, such as nitrogen or argon. The reaction mixture is preferably stirred for a period of time of up to about 3 days. In one embodiment, the reaction is carried out at a temperature of less than about 40° C., in another embodiment, at a temperature of less than about 35° C. and in yet another embodiment, at a temperature of less than about 30° C.

Preferably, the bidentate phosphine ligand is present in the reaction mixture in stoichiometric or excess molar quantities to the platinum group metal atom M. When the bidentate phosphine ligand is present in excess, it is calculated to provide a molar excess of preferably at least 1% over the amount required for the stoichiometric reaction.

Optionally, the PGM precursor compound may be present in combination with one or more solvents, such as ketones (e.g. acetone), alkyl ethers (for example, diethyl ether or MTBE, or cyclic alkyl ethers, such as tetrahydrofuran), aromatic hydrocarbons (e.g. toluene), alkyl cyanides (e.g. acetonitrile) or aryl cyanides (e.g. benzonitrile). In this embodiment, the solvent is selected such that the PGM precursor compound is soluble or partially soluble in the solvent whereas the complex of formula (A) or formula (B) has a limited solubility. Preferably, the solvent is degassed prior to combining it with the PGM precursor compound. In one embodiment, the PGM precursor compound is present in the solvent in a ratio of at least about 1 mmol PGM precursor compound per 1.6 ml of solvent and, in another embodiment, at least about 1 mmol of PGM precursor compound per 5 ml of solvent.

The PGM precursor compound may be selected from the group consisting of $MX_2$, $MX_2L_n$ and $[MXL_n]_2$, wherein M and X are as defined above, and when n is 1, L is a neutral bidentate ligand, or when n is 2, L is a neutral monodentate ligand. Neutral bidentate ligands include diolefins, more preferably cyclic diolefins, such as 2,5-norbornadiene (NBD) or 1,5-cyclooctadiene (COD). Neutral monodentate ligands include olefins, such as ethylene, $C_{5-10}$ cycloalkenes, such as cyclooctene, or solvent molecules, such as acetonitrile. Examples of $MX_2$, $MX_2L_n$ and $[MXL_n]_2$ complexes include $Pd(OAc)_2$, $PdCl_2$, $PdCl_2(COD)$, $PdBr_2(COD)$, $PdCl_2(MeCN)_2$, $PtCl_2(MeCN)_2$, $[IrCl(COD)]_2$ and $[RhCl(NBD)]_2$.

The method of the present invention is advantageous as heating at temperatures greater than about 40° C. may be avoided at all stages i.e. during the formation of the lithium salt of $R^1R^2PH$, the bidentate phosphine ligand and the complexes of formulae (A) and (B). In a preferred embodiment, step (a) and step (b) are independently carried out at one or more temperatures between about −10° C. and about 40° C. The method therefore is suited to large-scale manufacture and the complexes obtained are very pure.

In another embodiment, the process of the present invention further comprises the step of preparing a complex of formula (A') or formula (B'):

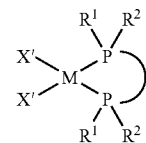 (A')

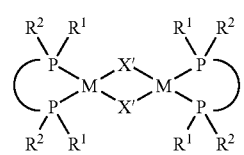 (B')

by independently exchanging one or more of the groups X for X',
wherein each X' is an anionic monodentate ligand which is different to the corresponding group X in the complex of formula (A) or formula (B).

The anion exchange may be conveniently carried by combining the complex of formula (A) or formula (B) with a YX' salt, wherein Y is an alkali metal cation (such as $K^+$ or $Na^+$) and X' is as defined above, in a solvent. The components may be combined in any suitable order, although it is preferred that the complex of formula (A) or formula (B) is combined with the YX' salt, followed by the addition of the solvent. Examples of suitable YX' salts include NaBr and NaI. Examples of suitable solvents include ketones, such as acetone. Preferably, the anion exchange is conducted under an inert atmosphere (such as argon or nitrogen).

In another aspect, the present invention provides a complex of formula (A), (B), (A') or (B') obtainable according to the processes as defined above.

On completion of the reaction, the complexes of formulae (A), (B), (A') or (B') may be separated from the reaction mixture by any appropriate method which is dependent on the physical form of the product. In particular, solid complexes may be recovered from the supernatant by filtering, decanting or centrifuging and optionally washed one or more times. If purification is necessary, the complexes may be obtained in high purity by conventional methods.

Howsoever the complex is recovered, the separated complex is preferably dried. Drying may be performed using known methods, for example, drying under an air stream or at temperatures in the range of 10-60° C. and preferably 20-40° C. under 0.1-30 mbar for 1 hour to 5 days.

The complexes prepared by the processes of the present invention are pure and may be used in catalytic applications as obtained or further dried.

The invention will be further illustrated by reference to the following non-limiting Examples.

EXAMPLES

The complexes were prepared using fresh reagents in an argon glove box.

Example 1

Preparation of $PdCl_2(dcpp)$

Di-cyclohexylphosphine (10% solution in hexane) (44 ml, 2.96 g $PHCy_2$, 15 mmol) was transferred to a 100 ml 3-necked flask under argon. Anhydrous THF (20 ml) was added. n-Butyl lithium (1.6M in hexane, 10 ml, 16 mmol) was added by syringe. The solution turned yellow/green but there was no immediate warming or precipitation. A pale precipitate began to form after a few minutes. Stirring was continued for 60 minutes, then 1,3-dichloropropane (0.70 ml, density 1.19, 7.4 mmol) was added slowly by pipette. Stirring was continued for 60 minutes.

Filter degassed water (10 ml) was added and the mixture shaken until all the solid had dissolved. The aqueous layer was removed. A second water wash (10 ml) was carried out and the organic phase was added to [$PdCl_2$(COD)] (2.0 g, 7.4 mmol) in 50 ml acetone, degassed.

The remaining suspended starting material began to dissolve and then a pale precipitate began to form. The mixture was stirred under argon overnight. The solid was collected by filtration and washed with hexane fraction. The powder was dried in an air stream.

Yield: 3.88 g (F. wt 613.7, 6.33 mmol, 85.5%)

The filtered solvent was evaporated to dryness and then triturated with hexane, and then toluene to yield a powder that was collected by filtration and dried in air.

Yield: 0.15 g (3.3% yield)

Example 2

Preparation of $PdCl_2$(dcpp)

The preparation of the complex was carried out under an inert atmosphere.

Di-cyclohexylphosphine (44 ml, 21.44 g $PHCy_2$, 108 mmol) was loaded in a Schlenk flask, 20 ml anhydrous hexane and 40 ml anhydrous THF were transferred into the flask. Under ice/water bath, n-Butyl lithium (1.6M in hexane, 56 ml, 90 mmol) was added by syringe. A pale precipitate began to form after a few minutes. Stirring was continued for 60 minutes under room temperature, then 1,3-dichloropropane (4 ml, 42 mmol) was added slowly by syringe under water/ice bath. Stirring was continued for 60 minutes under room temperature. The reaction mixture was then filtered with a frit covered with Celite (3 g). The filtrate was added into [$PdCl_2$(COD)] (10.84 g, 38 mmol) suspended in 60 ml degassed acetone. The remaining suspended starting material began to dissolve and then a pale precipitate began to form. The mixture was stirred under argon for 1.5 hours. The solid was collected by filtration and washed with 3×25 ml acetone and 20 ml hexane. The powder was dried under vacuum. Yield: 22.9 g (F. wt 613.7, 37.3 mmol, 98%)

Example 3

Preparation of $PdCl_2$($^iPrP(CH_2)_3P^iPr_2$)

Di-i-propylphosphine (10% solution in hexane) (9.8 ml, 0.59 g $PH^iPr_2$, 5 mmol) was transferred to a 100 ml 3-necked flask under argon and dry THF (5 ml) added. n-Butyl lithium (1.6M in hexane, 3.1 ml, 5 mmol) was added by syringe. The solution turned pale green but remained clear on stirring at room temperature. After ca. 20 minutes the mixture was cooled using an ice bath and some pale solid precipitated. 1,3-Dichloropropane (0.237 ml, 2.5 mmol) was added by pipette. Stirring was continued at 10° C. for 10 minutes and then the reaction was allowed to warm to room temperature. The white suspension was stirred for 3 hours.

Degassed water (5 ml) was added and the mixture shaken until all the solid had dissolved. The solution was then transferred to a separating funnel and the aqueous layer removed. The organic phase was added to [$PdCl_2$(COD)] (0.71 g, 2.5 mmol) in 20 ml acetone.

There was a rapid reaction and a pale precipitate formed. The mixture was stirred overnight. The solid was collected by filtration and washed with acetone. The powder was dried in an air stream.

Yield: 1.00 g 88%

A second small amount was recovered from the filtrate/wash liquor-0.09 g; Total yield ca. 97%

Example 4

Preparation of Pd(OAc)$_2$(dcpp)

Di-cyclohexylphosphine (10% solution in hexane) (44 ml, 2.96 g $PHCy_2$, 15 mmol) was transferred to a 100 ml 3-necked flask under argon. Anhydrous THF (20 ml) was added. n-Butyl lithium (1.6M in hexane, 10 ml, 16 mmol) was added by syringe. The solution turned yellow/green but there was no immediate warming or precipitation. A pale precipitate began to form after a few minutes. Stirring was continued for 30 minutes, and then the solution was cooled using an ice bath. After another 30 minutes 1,3-dichloropropane (0.70 ml, density 1.19, 7.4 mmol) was added slowly by pipette. Stirring was continued for 2 hours.

Filter degassed water (20 ml) was added and the mixture shaken until all the solid had dissolved. The aqueous layer was removed. The organic phase was added to [Pd(OAc)$_2$] (1.659 g, 7.4 mmol) in 50 ml acetone, degassed.

The mixture darkened to give a deep red solution with minimal solid. After stirring overnight this was transferred to a Buchi flask and evaporated under reduced pressure to give a red oil. This was stirred with hexane (ca. 100 ml) which was then decanted. This was repeated three times, finally stirring for 18 hours to give a pale yellow solid. The sample was chilled in the freezer before filtration. The solid was collected by filtration and dried in air and in vacuo.

Yield: 3.8 g (F. wt 661, 77% yield)

A similar preparation was carried out using toluene as solvent for Pd(OAc)$_2$ but in this case isolation was less effective (isolated yield 21%)

Example 5

Preparation of Pd(OAc)$_2$(Cy$_2$PCH$_2$CH$_2$CH(CH$_3$)PCy$_2$)

A solution of PCy$_2$H in hexane (10 wt %, 11 ml, 3.75 mmol) was transferred by syringe to a 100 ml round-bottomed flask. Anhydrous THF (ca. 5 ml) was added and then n-BuLi (2.5 ml, 1.6M in hexane, 4 mmol). The mixture was stirred for ca. 30 minutes at room temperature during which time a pale precipitate formed.

1,3-Dichlorobutane (211 microliters, 1.85 mmol) was added by pipette and stirring continued at room temperature for ca. 24 hours. The originally pale-green suspension became white.

Water (ca. 5 ml) was added and the mixture shaken to dissolve the precipitate and react excess lithium reagent. The aqueous phase was removed and the organic phase added to palladium acetate (0.414 g, 1.85 mmol) in acetone (ca. 20 ml). The mixture was stirred for 24 hours giving a deep red solution with a very small amount of suspended solid. The solution was filtered and the filtrate evaporated under reduced pressure to give an oil. This was re-dissolved in toluene and again evaporated to remove some of the water. The oil was then triturated with hexane. The organic solution was removed and the trituration repeated. Finally, the thick paste was dissolved in toluene and hexane added to give a cloudy solution. After stirring briefly at room temperature, initiating the formation of solid, the solution was placed in the freezer overnight. After warming to room temperature the solid was collected by filtration and dried in air.

Yield: 0.225 g

The filtrate was re-evaporated to low volume and again diluted with hexane and stored in the freezer to yield a second crop.

Yield: 0.132 g

Example 6

Preparation of $PdCl_2({}^iBu_2P(CH_2)_3P^iBu_2)$

Di-i-butylphosphine (10% solution in hexane) (22 ml, 1.46 g $PH^iBu_2$, 10 mmol) was transferred to a 100 ml 3-necked flask under argon. Anhydrous THF (5 ml) was added. n-Butyl lithium (1.6M in hexane, 6.3 ml, 10 mmol) was added by syringe. The pale green solution was stirred for 20 minutes and then cooled using an ice bath. There was no precipitate. 1,3-Dichloropropane (0.475 ml, 5.0 mmol) was added by pipette. This caused the immediate formation of a pale precipitate. Stirring was continued for ca. 3 hours as the reaction was allowed to warm to ambient temperature.

Filtered, degassed water (10 ml) was added and the mixture shaken until all the solid had dissolved. The solution was then transferred to a separating funnel and the aqueous layer removed. The organic phase was added to $[PdCl_2]$ (0.88 g) in MeCN (20 ml) previously heated to reflux for 1 hour.

A pale green solution was formed but there was no precipitation. Two liquid phases remained so the mixture was stirred vigorously over a weekend to allow reaction to occur. No precipitate was formed.

The mixture was evaporated under reduced pressure, which caused the product to precipitate. The solid was re-suspended in hexane fraction and stirred. The mixture was then filtered and the product dried in an air stream.

Yield: 2.45 g $[PdCl_2(di-i-bpp)]$ (96%)

Example 7

Preparation of $PdCl_2(Cy_2P(CH_2)_4PCy_2)$

Di-cyclohexylphosphine (10% solution in hexane) (22 ml, 1.48 g $PHCy_2$, 7.5 mmol) was transferred to a 100 ml 3-necked flask under argon. Anhydrous THF (8 ml) was added. n-Butyl lithium (1.6M in hexane, 5 ml, 8 mmol) was added by syringe. There was some initial clouding but no immediate warming or precipitation. A pale precipitate was formed on stirring for a few minutes. Stirring was continued while cooling in an ice bath. The reaction was cooled to ca. 5° C. and then 1,4-dichlorobutane (0.41 ml, 3.7 mmol) was added by pipette. Stirring was continued in the ice bath for 10 minutes and then the reaction was allowed to warm to room temperature. Stirring was continued for 4 hours.

Filter degassed water (10 ml) was added and the mixture shaken until all the solid had dissolved. The aqueous layer was removed and the organic phase was added to $[PdCl_2(MeCN)_2]$ solution/suspension, which was prepared by heating 0.62 g (3.5 mmol) $PdCl_2$ in 20 ml MeCN for 1 hour.

The remaining suspended starting material began to dissolve and very slowly a pale precipitate began to form. The mixture was stirred under argon overnight.

The solid was collected by filtration and washed with acetone. The powder was dried in an air stream.

Yield: 1.837 g (83.6%, based on Pd) $[PdCl_2(dcpb)]$

Example 8

Preparation of $PdBr_2(dcpp)$ $PdCl_2(dcpp)$ (0.3 g) and sodium bromide (0.3 g) were weighed into a flask. Under argon 10 ml acetone (10 ml) was added and the mixture stirred for 2 days. The suspension was diluted with water (ca. 10 ml) and then filtered. The product was washed with water and methanol and dried in vacuo.

Yield: 0.306 g

Samples of complexes $PdX_2$(diphosphine) may also be prepared by use of a Pd precursor containing the appropriate halide. Thus, for example, bromide complexes can be prepared using $PdBr_2(COD)$.

Example 9

Preparation of $PdI_2(dcpp)$ $PdCl_2(dcpp)$ (0.3 g) and sodium iodide (0.3 g) were weighed into a flask. Under argon 10 ml acetone (10 ml) was added and the mixture stirred for 2 days. The suspension was diluted with water (ca. 10 ml) and then filtered. The product was washed with water and methanol and dried in vacuo.

Yield: 0.347 g

Example 10

Preparation of $[RhCl(dcpp)]_2$

Di-cyclohexylphosphine (10% solution in hexane, 11 ml, 0.74 g $PHCy_2$, 3.75 mmol) was transferred to a 100 ml 3-necked flask under argon. Anhydrous THF (5 ml) was added. n-Butyl lithium (1.6M in hexane, 2.5 ml, 4 mmol) was added by syringe. The solution turned yellow/green but there was no immediate warming or precipitation. A pale precipitate began to form after a few minutes. Stirring was continued for 50 minutes, then 1,3-dichloropropane (0.18 ml, density 1.19, 1.89 mmol) was added slowly by pipette. Stirring was continued for 3 hours.

The solution was then transferred to a separating funnel and filter degassed water (5 ml) was added and the mixture shaken until all the solid had dissolved. The aqueous layer was removed. The organic phase was added to $[RhCl(nbd)]_2$ (0.426 g, 0.925 mmol dimer) in 10 ml acetone, degassed.

The remaining suspended starting material began to dissolve and then a pale precipitate began to form rapidly. The mixture was stirred under argon overnight. The solid was collected by filtration and washed with hexane fraction. The powder was dried in an air stream.

Yield: 0.917 g (F. wt 1150, 0.798 mmol, 86%)

Example 11

Preparation of $[IrCl(dcpp)]_2$ and $PtCl_2(dcpp)$

Di-cyclohexylphosphine (10% solution in hexane, 22 ml, 1.48 g $PHCy_2$, 7.5 mmol) was transferred to a 100 ml 3-necked flask under argon. Anhydrous THF (10 ml) was added. n-Butyl lithium (1.6M in hexane, 5 ml, 8 mmol) was added by syringe. The solution turned yellow/green but there was no immediate warming or precipitation. A pale precipitate began to form after a few minutes. Stirring was continued for 10 minutes, then the solution was cooled using an ice bath. After 40 minutes, 1,3-dichloropropane (0.36 ml, density 1.19, 3.78 mmol) was added by pipette. The ice bath was removed and the mixture was stirred overnight.

The solution was then transferred to a separating funnel and filter degassed water (10 ml) was added and the mixture shaken until all the solid had dissolved. The aqueous layer was removed. The organic phase was separated into two equal portions and added to:
1. [IrCl(COD)]$_2$ 0.62 g, 0.925 mmol dimer in 20 ml acetone, degassed
2. [PtCl$_2$(MeCN)$_2$] 0.64 g 1.85 mmol in 20 ml acetone, degassed The remaining suspended starting material began to dissolve and then a pale precipitate began to form (white for platinum, pale brown for Ir). The mixtures were stirred under argon overnight. The solids were collected by filtration and washed with hexane fraction. The powders were dried in an air stream.

Yield: 1.028 g (F. wt. 1328, 0.775 mmol, 84%)
Yield: 1.106 g (F. wt. 703, 1.575 mmol, 85%)
Analytical Data

Elemental Analysis[a]

| Compound[c,d] | | Pd | Cl | P | C | H |
|---|---|---|---|---|---|---|
| PdCl$_2$(d$^i$ppp) | Exp | 23.46 | 15.63 | 13.66 | 39.68 | 7.56 |
| | Found | | 16.03 | | 39.81 | 7.65 |
| PdCl$_2$(d$^i$ppb) | Exp | 22.75 | 15.16 | 13.25 | 41.06 | 7.76 |
| | Found | | 15.23 | | 40.76 | 7.36 |
| PdCl$_2$(d$^i$bpp) | Exp | 20.88 | 13.91 | 12.16 | 44.74 | 8.31 |
| | Found | | 14.18 | | 44.72 | 8.60 |
| PdCl$_2$(d$^t$bpp) | Exp | 20.88 | 13.91 | 12.16 | 44.74 | 8.31 |
| | Found | | 14.08 | | 45.03 | 8.38 |
| PdCl$_2$(d$^t$bpb) | Exp | 20.32 | 13.54 | 11.83 | 45.83 | 8.47 |
| | Found | | 13.81 | | 44.80 | 8.06 |
| PdCl$_2$(dcpp) | Exp | 17.34 | 11.55 | 10.09 | 52.79 | 8.21 |
| | Found | | 11.62 | | 52.93 | 8.04 |
| PdCl$_2$(dcpb) | Exp | 16.95 | 11.29 | 9.87 | 53.53 | 8.35 |
| | Found | | 11.81 | | 52.95 | 8.07 |
| PdCl$_2$(d(cyp)pp) | Exp | 19.08 | 12.71 | 11.11 | 49.49 | 7.59 |
| | Found | | 12.32 | | 50.07 | 7.83 |
| PdCl$_2$(d(cyp)pb) | Exp | 18.61 | 12.40 | 10.84 | 50.38 | 7.76 |
| | Found | | 11.94 | | 51.79 | 7.93 |
| PdCl$_2$(d(nbn)pp) | Exp | 16.08 | 10.71 | 9.36 | 56.22 | 7.62 |
| | Found | | 10.81 | | 56.28 | 7.68 |
| PdBr$_2$(d$^i$ppp) | Exp | 19.61 | 29.47 | 11.42 | 33.18 | 6.32 |
| | Found | | 29.10 | | 33.73 | 6.41 |
| PdBr$_2$(d$^t$bpp) | Exp | 17.78 | 26.72 | 10.35 | 38.09 | 7.07 |
| | Found | | 26.68 | | 38.06 | 7.01 |
| PdBr$_2$(d$^t$bpb) | Exp | 17.37 | 26.10 | 10.11 | 39.18 | 7.24 |
| | Found | | 25.95 | | 39.24 | 7.19 |
| PdBr$_2$(d$^i$bpp) | Exp | 17.78 | 26.72 | 10.35 | 38.09 | 7.07 |
| | Found | | 26.78 | | 38.81 | 7.39 |
| PdBr$_2$(d$^i$ppb) | Exp | 19.12 | 28.73 | 11.13 | 34.50 | 6.52 |
| | Found | | 28.50 | | 34.35 | 6.44 |

Data provided by Analytical Service, Strathclyde University, UK.

$^{31}$P NMR spectral data for bisphosphine palladium catalysts[a]

| Formula[c,d] | δ/ppm |
|---|---|
| PdCl$_2$(dppp) | 11.8 |
| PdBr$_2$(dppp) | 8.2 |
| PdCl$_2$(d$^i$ppp) | 37.7 |
| PdBr$_2$(d$^i$ppp) | 36.4 |
| PdBr$_2$(d$^i$bpp) | 9.3 |
| PdBr$_2$(d$^t$bpp) | 42.1 |
| PdCl$_2$(d(cyp)pp) | 24.6 |
| PdCl$_2$(dcpp) | 33.2 |
| PdCl$_2$(d(nbn)pp) | m, 29–34[b] |
| PdCl$_2$(dppb) | 29.2 |
| PdBr$_2$(d$^i$ppb) | 51.4 |
| PdBr$_2$(d$^t$bpb) | 41.2 |
| PdCl$_2$(d(cyp)pb) | 39.0 |

Elemental Analysis[a]

[a]Values reported relative to 85% H$_3$PO$_4$ in external capillary. Spectra recorded at 109.365 MHz. Samples prepared as saturated solutions in deuterochloroform.
[b]Complex multiplet due to presence of exo- and endo-isomers.
[c]The complexes listed were made according to the procedures detailed in Examples 1, and 3 to 11.
[d]dppp = bis(diphenylphosphanyl)propane
d$^i$ppp = bis(di-isopropylphosphanyl)propane
d$^i$bpp = bis(di-isobutylphosphanyl)propane
d$^t$bpp = bis(di-tertiary-butylphosphanyl)propane
dcpp = bis(dicyclohexylphosphanyl)propane
d(cyp)pp = bis(dicyclopentylphosphanyl)propane
d(nbn)pp = bis(dinorbornylphosphanyl)propane
dcpb = bis(dicyclohexylphosphanyl)butane
dppb = bis(diphenylphosphanyl)butane
d$^i$ppb = bis(di-isopropylphosphanyl)butane
d$^t$bpb = bis(di-tertiary-butylphosphanyl)butane
d(cyp)pb = bis(dicyclopentylphosphanyl)butane

What is claimed is:

1. A process for the preparation of a complex of formula (A) or (B):

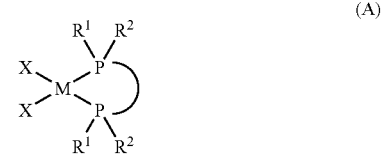

wherein,
M is a platinum group metal atom;
each X is an anionic monodentate ligand;

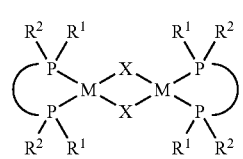

is a bidentate phosphine ligand; and
R$^1$ and R$^2$ are independently selected from the group consisting of straight-chain C$_{1-10}$ alkyl, branched-chain C$_{3-10}$ alkyl, C$_{3-10}$ cycloalkyl and optionally substituted aryl;
comprising the steps of:
(a) preparing

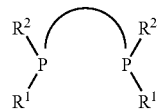

by reacting the lithium salt of R$^1$R$^2$PH with a dihaloalkane in a solvent comprising an alkyl ether and, optionally, an alkane, provided the alkyl ether is not diethyl ether;
(b) reacting

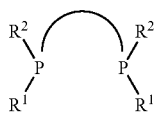

with a platinum group metal precursor compound to form the complex of formula (A) or formula (B), wherein the

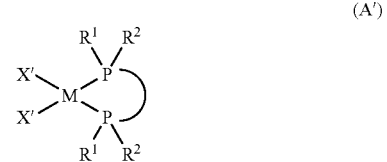

is not isolated before it is reacted with the platinum group metal precursor compound.

2. A process according to claim 1, wherein M is selected from the group consisting of ruthenium, rhodium, palladium, osmium, iridium and platinum.

3. A process according to claim 1, wherein each X is independently selected from the group consisting of chloride, bromide, iodide and acetate.

4. A process according to claim 1, wherein $R^1$ and $R^2$ are independently selected from the group consisting of methyl, ethyl, n-propyl, i-propyl, n-butyl, i-butyl, t-butyl, cyclopentyl, cyclohexyl, norbornyl and phenyl.

5. A process according to claim 1, wherein the alkyl ether is a cyclic alkyl ether.

6. A process according to claim 1, wherein the alkyl ether is methyl tert-butyl ether or tetrahydrofuran.

7. A process according to claim 1, wherein the alkane has a boiling point at atmospheric pressure between about 0° C. and about 150° C.

8. A process according to claim 1, wherein the alkane is selected from the group consisting of pentane isomers, hexane isomers, heptane isomers and octane isomers.

9. A process according to claim 1, wherein the platinum group metal precursor compound is selected from the group consisting of $MX_2$, $MX_2L_n$ and $[MXL_n]_2$, wherein M and X are as defined in claim 1, and
when n is 1, L is a neutral bidentate ligand, or
when n is 2, L is a neutral monodentate ligand.

10. A process according to claim 1, wherein step (a) and step (b) are independently carried out at one or more temperatures between about −10° C. and about 40° C.

11. A process according to claim 1, further comprising:
(a') treating the reaction mixture obtained after step (a) one or more times with water and discarding the aqueous layer(s).

12. A process according to claim 1, further comprising the step of preparing a complex of formula (A') or formula (B'):

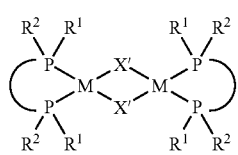

by independently exchanging one or more of the groups X for X',
wherein each X' is an anionic monodentate ligand which is different to the corresponding group X in the complex of formula (A) or formula (B).

13. A process according to claim 1, wherein the dihaloalkane has the formula Hal-$(CR^5R^6)_m$—Hal wherein Hal is a halide,
m is 2, 3 or 4, and
$R^5$ and $R^6$ are independently selected from the group consisting of H, straight-chain $C_{1-10}$ alkyl, branched-chain $C_{3-10}$ alkyl, and $C_{3-10}$ cycloalkyl.

14. A process according to claim 13, wherein the dihaloalkane is selected from the group consisting of 1,3-dichloropropane, 1,4-dichlorobutane and 1,3-dichlorobutane.

* * * * *